(12) United States Patent
Meckes et al.

(10) Patent No.: US 9,883,796 B2
(45) Date of Patent: Feb. 6, 2018

(54) OPHTHALMOLOGIC SYSTEM AND METHOD OF OPERATING THE SAME

(71) Applicant: Carl Zeiss Meditec AG, Jena (DE)

(72) Inventors: Günter Meckes, München (DE); Konstantinos Filippatos, München (DE); Thomas Schuhrke, München (DE); Christoph Hauger, Aalen (DE); Abouzar Eslami, München (DE); Stefan Gräber, Deisenhofen (DE); Christine Kochwagner, Rott am Inn (DE); Carolin Schiele, Aufhausen (DE); Christopher Käsbach, Aalen (DE)

(73) Assignee: CARL ZEISS MEDITEC AG, Jena (DE)

( * ) Notice: Subject to any disclaimer, the term of this patent is extended or adjusted under 35 U.S.C. 154(b) by 314 days.

(21) Appl. No.: 14/873,337

(22) Filed: Oct. 2, 2015

(65) Prior Publication Data

US 2016/0095514 A1 Apr. 7, 2016

(30) Foreign Application Priority Data

Oct. 2, 2014 (DE) .................. 10 2014 014 705

(51) Int. Cl.
*A61B 3/15* (2006.01)
*A61B 3/113* (2006.01)
(Continued)

(52) U.S. Cl.
CPC .............. *A61B 3/102* (2013.01); *A61B 3/113* (2013.01); *A61B 3/13* (2013.01); *A61B 3/14* (2013.01); *A61B 3/152* (2013.01)

(58) Field of Classification Search
CPC A61B 3/102; A61B 3/113; A61B 3/13; A61B 3/14; A61B 3/152
(Continued)

(56) References Cited

U.S. PATENT DOCUMENTS

2011/0202017 A1 8/2011 Reimer
2013/0093997 A1 4/2013 Utsunomiya et al.
(Continued)

FOREIGN PATENT DOCUMENTS

DE 10 2010 008 146 A1 8/2011

OTHER PUBLICATIONS

Spectralis, "Anterior Segment Module," Heidelberg Engineering GmbH, 2011, pp. 1-2, (http://www.heidelbergengineering.com.international/wp-content/uploads/2011/09/SPECTRALIS_Insert_anteriorSEG_2_engl_web.pdf).
(Continued)

*Primary Examiner* — Thomas K Pham
*Assistant Examiner* — Mitchell Oestreich
(74) *Attorney, Agent, or Firm* — Patent Portfolio Builders PLLC (57) ABSTRACT

An ophthalmologic system comprising and eye tracker and an OCT system. A method of operating the ophthalmologic system comprises: providing data representing a placement of a first B-scan performed on an eye relative to the eye; performing a measurement on the eye using the eye tracker; determining a placement of the eye relative to the ophthalmologic system based on the measurement using the eye tracker; placing the eye relative to a reference placement of the OCT system based on the provided data and the determined placement; performing A-scans on the eye at at least three A-scan positions; determining a placement of a second B-scan relative to the OCT system based on at least one of the at least three A-scans and the provided data such that the second B-scan and the first B-scan have a substantially same placement relative to the eye; and generating a representation of the second B-scan.

15 Claims, 4 Drawing Sheets

(51) Int. Cl.
 *A61B 3/14* (2006.01)
 *A61B 3/13* (2006.01)
 *A61B 3/10* (2006.01)

(58) Field of Classification Search
 USPC ........................................................ 351/208
 See application file for complete search history.

(56) References Cited

U.S. PATENT DOCUMENTS

2013/0188140 A1  7/2013  Bagherinia et al.
2015/0109579 A1* 4/2015  Orlowski .............. A61B 3/102
                                                 351/206

OTHER PUBLICATIONS

Spectralis, "TruTrack Active Eye Tracking," Heidelberg Engineering GmbH, 2011, pp. 1, (http://www.heidelbergengineering.com/international/company/technologies/trutrack-active-eye-tracking/).
German Office Action, with translation thereof, for corresponding DE application No. 10 2014 014 705.3 dated Jun. 19, 2015.

* cited by examiner

OPHTHALMOLOGIC SYSTEM AND METHOD OF OPERATING THE SAME

CROSS-REFERENCES TO RELATED APPLICATIONS

The present application claims priority of Patent Application No. 10 2014 014 705.3, filed Oct. 2, 2014 in Germany, the entire contents of which are incorporated by reference herein.

FIELD

The invention relates to ophthalmologic systems and method of operating of ophthalmologic systems. The invention in particular relates to ophthalmologic systems including an OCT system.

BACKGROUND

OCT systems use the technique of the optical coherence tomography and are used in ophthalmology for obtaining information related to structures in the interior of an eye in a noninvasive manner. This information can be represented as one or more images. For this purpose, a focused beam of OCT measuring light is directed onto the eye such that it enters into the eye at a desired position on the eye surface. Measuring light reflected or scattered at locations within the interior of the eye is detected and analyzed in order to determine the light reflectivity or scattering probability of the structures of the eye in dependence of the depth within a depth range. A measurement of the depth dependent reflectivity along a line entering the eye at a given position is referred to as an A-scan in the art. When a plurality of such A-scans is performed at different positions distributed along a line, the reflectivity can be determined in dependence of depth and position along the line such that reflectivities can be determined within a delimited portion of a plane. Such measurement is referred to as a B-scan in the art. Data representing the reflectivities within the portion of the plane can be represented as two-dimensional images in which locations having high reflectivities are represented to the eye of the user at higher intensities, for example, and locations having smaller reflectivities are presented at lower intensities.

An ophthalmologic system including an OCT system and used for diagnosing a deficiency of an eye can be used to perform a B-scan along a plane having a desired placement relative to the eye of a patient. The plane can be selected such that it intersects a region of the eye including a suspected deficiency wherein it is intended to treat the deficiency by a subsequent surgery. One example for such deficiency at a given location of the eye is the region of the chamber angle of a patient having developed a glaucoma. The subsequent surgery can be performed using a surgical microscope having an integrated OCT system. It is then possible to examine the region of the eye having developed the deficiency using the OCT system integrated with the surgical microscope by performing a further B-scan. A strategy of performing the surgery can be developed based on a representation of this B-scan. It is further possible to perform further OCT scans during the surgery in order to verify a success of subsequent steps of the surgery and to adapt the strategy. Herein, it is desirable that the plane along which the OCT scan is performed during the surgery coincides with the plane along which the pre-operative B-scan using the diagnostic OCT system has been performed.

Conventionally, the user of the surgical microscope tries to manually adjust a placement of the B-scan relative to the eye such that this placement substantially corresponds to the pre-operative B-scan obtained using the diagnostic OCT system. This requires substantial effort and can be achieved only with a limited accuracy since the position and orientation of the eye relative to the OCT system of the surgical microscope is not defined with a sufficient accuracy. It is further desirable that the B-scans performed using the OCT system of the surgical microscope during the surgery coincide with previously obtained B-scans using the same OCT system. This is, however, also difficult to achieve since the eye is moved during the surgery such that placements of subsequent B-scans relative to the eye cannot be readily reproduced.

Therefore, it is desirable to provide a method of operating an ophthalmologic system including an OCT system allowing to represent B-scans obtained along planes corresponding to previously performed B-scans.

SUMMARY

The present invention has been achieved taking the above considerations into account.

According to embodiments of the present invention, the ophthalmologic system comprises an OCT system and an eye tracker.

According to some embodiments, a method of operating the ophthalmologic system comprises providing data representing a placement of a first B-scan performed on an eye relative to the eye; performing a measurement on the eye using the eye tracker; determining a placement of the eye relative to the ophthalmologic system based on the measurement using the eye tracker; placing the eye relative to a reference placement of the OCT system based on the provided data and the determined placement; performing A-scans on the eye at at least three A-scan positions, wherein the at least three A-scan positions are not arranged on one straight line; determining a placement of a second B-scan relative to the OCT system based on at least one of the at least three A-scans and the provided data such that the second B-scan and the first B-scan have a substantially same placement relative to the eye; and generating a representation of the second B-scan.

In the context of the present application, the placement of a B-scan relative to the eye should be understood as explaining the placement of a plane relative to the eye wherein this plane includes a portion with locations at which scattering intensities are determined by a plurality of A-scans forming a B-scan. Generally, this portion of a plane has a shape of a rectangle having an edge of a length corresponding to a depth measuring range of the OCT system, wherein the other edge has a length corresponding to a length of the line along which the B-scan is performed.

Based on the determined placement of the eye relative to the ophthalmologic system and the data representing the placement of the first B-scan relative to the eye, it is possible to place the eye at a reference placement relative to the OCT system. For this purpose, it is possible to displace the ophthalmologic system in space when the patient rests on a fixed support. Alternatively, actuators of a stand carrying the ophthalmologic system can be operated. Moreover, deflecting mirrors of the OCT system or a null or starting position of a scan mirror of the OCT system can be adjusted such that the reference placement of the OCT system is changed relative to the eye tracker in order to move the reference placement of the OCT system relative to the eye.

According to exemplary embodiments, the method comprises performing of A-scans at at least three A-scan positions, wherein these A-scan positions are not located on a common straight line. The at least three A-scan positions can be determined, for example, based on the provided data and/or the determined placement of the eye relative to the ophthalmologic system. These A-scans can be analyzed in order to determine the placement of the eye relative to the OCT system with a higher accuracy. Based on the at least three A-scans and/or the provided data the placement of a second B-scan can be determined relative to the eye and which substantially corresponds to the placement of the first B-scan relative to the eye. A representation of this second B-scan can be generated.

According to exemplary embodiments, the method further comprises performing a third B-scan having a same placement relative to the eye than the second B-scan, wherein information obtained from performing the third B-scan is used for generating the representation of the second B-scan and to generate a representation of the second B-scan. Herein, the placement of the eye relative to the OCT system can be first determined using the eye tracker, and the determination of the placement of the eye relative to the OCT system can then be determined with a higher accuracy using the at least three A-scans. It is then possible to perform the third B-scan such that it has a placement relative to the eye corresponding to the second B-scan which is desired to be represented. Therefore, the performed third B-scan has the substantially same placement relative to the eye as the first B-scan, and the performed third B-scan can be represented as the desired second B-scan. Herein, it is also possible to perform plural third B-scans and to generate the representation of the second B-scan by averaging the plural third B-scans, for example.

According to further exemplary embodiments, a plurality of A-scans is performed, wherein the A-scans have a hull volume which contains at least a portion of the second B-scan whose representation is to be generated. The hull volume is a volume defined in space having a convex hull of those locations at which reflectivities are measured in the A-scans.

According to exemplary embodiments herein, the generating of the representation of the second B-scan comprises representing of scattering intensities at a plurality of locations. The representation of scattering intensities at each given location of the plurality of locations of the second B-scan is generated based on a subset of measured scattering intensities, wherein the measured scattering intensities are obtained by performing the plurality of A-scans. By performing the plurality of A-scans, scattering intensities are also obtained at a plurality of locations. Among the total set of locations at which scattering intensities have been measured by the plurality of A-scans, scattering intensities measured at a subset of these locations contribute to the representation of the scattering intensities at the given location of the second B-scan. The locations of this subset have a distance from the given location which is smaller than a predetermined distance. This means that the representation of scattering intensities at each given location of the plurality of locations of the second B-scans is generated based on measured scattering intensities obtained by the plurality of A-scans at locations having a small or no distance from the given location.

This allows to generate a representation of the second B-scan which is not based on performing a B-scan having a substantially same placement relative to the eye as the desired second B-scan. Moreover, the representation of the second B-scan is generated from a plurality of A-scans performed in a surroundings of the desired second B-scan. In particular, plural A-scans may intersect the plane of the second B-scan at different locations. Such generation of the representation of the second B-scan may be advantageously used if it is not possible to place the eye relative to the OCT system such that the OCT system may perform a B-scan having a placement relative to the eye which is substantially identical to the placement relative to the eye of the first B-scan. In other words, it is possible to generate a representation of a B-scan corresponding to the first B-scan without performing such B-scan itself.

According to exemplary embodiments, the hull volume has a shape of a cuboid. Herein, the plurality of A-scans may be obtained as a plurality of B-scans recorded along parallel adjacent straight lines such that the A-scan positions are arranged in a rectangular array. This allows to obtain information relating to structures of the eye within a cuboid region containing at least a portion of the region scanned with the first B-scan. Based on the scattering data obtained from the cuboid region, it is possible to generate a representation of the second B-scan having a placement relative to the eye corresponding or equal to the placement of the first B-scan relative to the eye. The scattering data associated with the individual locations obtained by scanning the cuboid regions are data elements which can be also referred to as voxels. These voxels have positions relative to the eye which generally do not exactly correspond with the positions of the scattering data elements of the first B-scan. However, the data elements used for the representation of the second B-scan can be obtained from voxels located close or near to the respective data elements of the first B-scan. The values of a set of voxels located within a small distance from a given data element of the representation of the second B-scan can be, for example, averaged in order to calculate a value of the data element of the representation of the second B-scan.

According to exemplary embodiments, the eye tracker comprises a surgical microscope and a camera, and the determining of the placement of the eye relative to the ophthalmologic system may be based on images detected by the camera. The surgical microscope can be used by the surgeon for performing the surgery.

According to exemplary embodiments, the provided data represent the placement of the first B-scan relative to the eye with respect to at least four and, in particular, six degrees of freedom, wherein the degrees of freedom can be represented by plural parameters. These parameters may comprise a position in an x-direction, a position in a y-direction, by rotation a magnification and/or a tilt. According to exemplary embodiments herein, the placement of the eye relative to the ophthalmologic system as measured using the eye tractor is determined with respect to at least three, and in particular, four degrees of freedom. These at least three degrees of freedom can be represented by a position in the x-direction, the position in the y-direction, the rotation and/or the magnification.

According to further exemplary embodiments, the placement of the eye relative to the ophthalmologic system obtained from the at least three A-scans can be determined with respect to at least one degree of freedom including the tilt.

Embodiments of the present invention provide an ophthalmologic system configured to perform the method illustrated above.

BRIEF DESCRIPTION OF THE DRAWINGS

The forgoing as well as other advantageous features of the disclosure will be more apparent from the following detailed description of exemplary embodiments with reference to the accompanying drawings. It is noted that not all possible embodiments necessarily exhibit each and every, or any, of the advantages identified herein.

DETAILED DESCRIPTION OF EXEMPLARY EMBODIMENTS

In the exemplary embodiments described below, components that are alike in function and structure are designated as far as possible by alike reference numerals. Therefore, to understand the features of the individual components of a specific embodiment, the descriptions of other embodiments and of the summary of the disclosure should be referred to.

Figure 1:
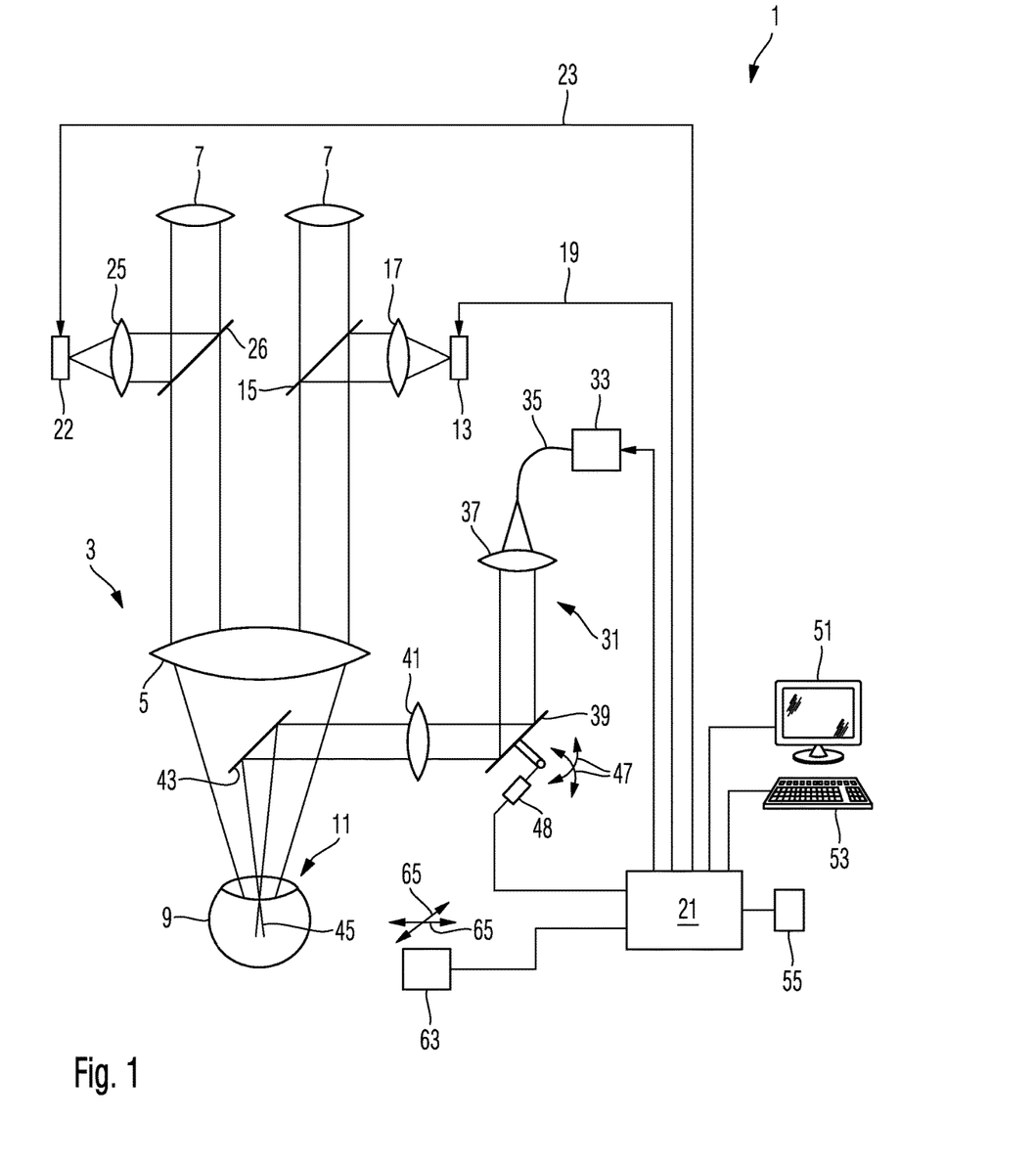
FIG. 1 is a schematic representation of an ophthalmologic system.

FIG. 1 shows a schematic illustration of an ophthalmologic system 1 for examining an eye 9 of a patient and for performing a surgery on that eye. The ophthalmologic system 1 comprises a surgical microscope 3 having an objective lens 5 and two oculars 7 into which the user can look with his eyes in order to see a stereoscopic image of an anterior portion 11 of the eye 9. The surgical microscope 3 further comprises a camera 13 for detecting images of a same region of the eye 9 which the user will see when looking into the ocular 7. For this purpose, a semitransparent mirror 15 can be arranged in a beam path between the objective lens 5 and one of the oculars 7. The semitransparent mirror 15 directs a portion of the light from the beam path towards the ocular 7, via adapter optics 17, to the camera 13. The images detected by the camera 13 are transferred as image data via a date line 19 to a controller 21. While the surgical microscope 3 of the illustrated example has only one camera 13, it is apparent that a further camera can be provided which detects light from the beam path towards the other ocular 7, such that both cameras together may detect stereoscopic images of the eye 9. These images can be supplied to a stereoscopic display, such as a head mounted display. The user may then perceive stereoscopic images of the eye 9 while looking at the stereoscopic display rather than into the oculars. It is further apparent that an ophthalmologic system having a display for displaying the recorded images of the camera does not require oculars, which may then be omitted.

The surgical microscope 3 further comprises an image display 22 displaying images received from the controller 21 via a data line 23. The displayed images are projected via projection optics 25 towards a semitransparent mirror 26 arranged in a beam path between the objective lens 5 and the ocular 7 such that the user may see the images displayed by the image display 22 when looking into the ocular 7.

The ophthalmologic system 1 further comprises an OCT system 31 including on interferometer 33 controlled by the controller 21. The interferometer 33 outputs measuring light from a fiber 35. The measuring light emitted from an end of the fiber 35 is collimated by optics 37, reflected from a scan mirror 39 and is focused by optics 41 such that a focus of the measuring light beam is produced within the eye 9 subsequent to a reflection at a mirror 43 disposed between the objective lens 5 and the eye 9. Other configurations of the OCT system 31 are possible. For example, the OCT measuring light beam may traverse the objective lens 5. The scanning mirror 39 is rotable about two independent axes as indicated by arrows 47 in FIG. 1. The rotational position of the mirror 39 is controlled by an actuator 48 controlled by the controller 21. Other configurations for deflecting the OCT measuring light beam are possible. For example, the OCT measuring light beam may be reflected from two subsequent mirrors, wherein each mirror is rotable about one axes and controlled by a respective actuator controlled by the controller 21. The controller 21 controls the actuator 48 in order to change a position at which the measuring light beam traverses the surface of the eye. This position can be independently controlled in two spatial directions (x, y).

A portion of the measuring light directed into the eye is scattered or reflected at structures within the eye and traverses the illustrated beam path in the reverse direction, i.e. it is reflected from the mirror 43, traverses the optics 41, is reflected from the scanning mirror 39, traverses the optics 37 and enters into the fiber 35. This light returning to the interferometer 33 is detected by the interferometer 33 according to the principles of optical coherence tomography (OCT) such that the data generated by the interferometer 33 and transmitted to the controller 21 represent a depth profile of a light reflectivity or scattering probability of structures of the eye 9. These data are also referred to as an A-scan in the art.

By operating the scanning mirror 39, the measuring light beam can be directed to a plurality of positions distributed along a straight line on the eye in order to obtain an A-scan at each position. The measuring data obtained from the plurality of A-scans represent light reflectivities or scattering probabilities of the structures of the eye along a sectional plane. Such plurality of A-scans obtained along a line is also referred to as a B-scan in the art.

The obtained B-scans can be displayed by the controller 21 on the display 51, for example. Moreover, the B-scans can also be displayed on the image display 22 such that the user may see the B-scan together with the image of the eye 9 when looking into the ocular. The controller 21 is controlled by the user using a suitable input device, such as a keyboard 53.

Using the illustrated ophthalmologic system, it is possible to perform B-scans on the eye 9 along selectable B-scan lines and to display the performed B-scans before and during the surgery on the eye 9. Herein, it is desirable that the subsequent B-scans always have a same placement relative to the eye 9 such that a progress and success of the surgery can be determined by comparing representations of the B-scans. However, this is not always possible since the eye 9 is moved during the surgery such that a placement of the eye relative to the ophthalmologic system 1 is changed. Moreover, it is desirable to perform B-scans using the ophthalmologic system 1 which have a placement relative to the eye 9 which is similar or identical to a B-scan performed on the eye before the surgery and using a different OCT system, such as an OCT system used for diagnosing an eye defect at a distant place, such as in the premises of an ophthalmologist. This is generally also not possible since the placement of the eye relative to the other OCT system was probably different from the placement of the eye relative to the ophthalmologic system at a given moment. The methods illustrated below are useful for generating a representation of a B-scan having a placement relative to the eye similar or identical to a previously performed B-scan.

The controller 21 has a data interface 55 for inputting data representing a placement of the eye relative to another OCT system which was previously used to perform a B-scan of the eye. The ophthalmologic system 1 may then generate a representation of a B-scan having a placement relative to the eye corresponding or identical to the placement of the eye represented by the data received via the data interface 55. The placement of the B-scan relative to the eye may be represented, for example, in a coordinate system of the eye.

Figure 2:
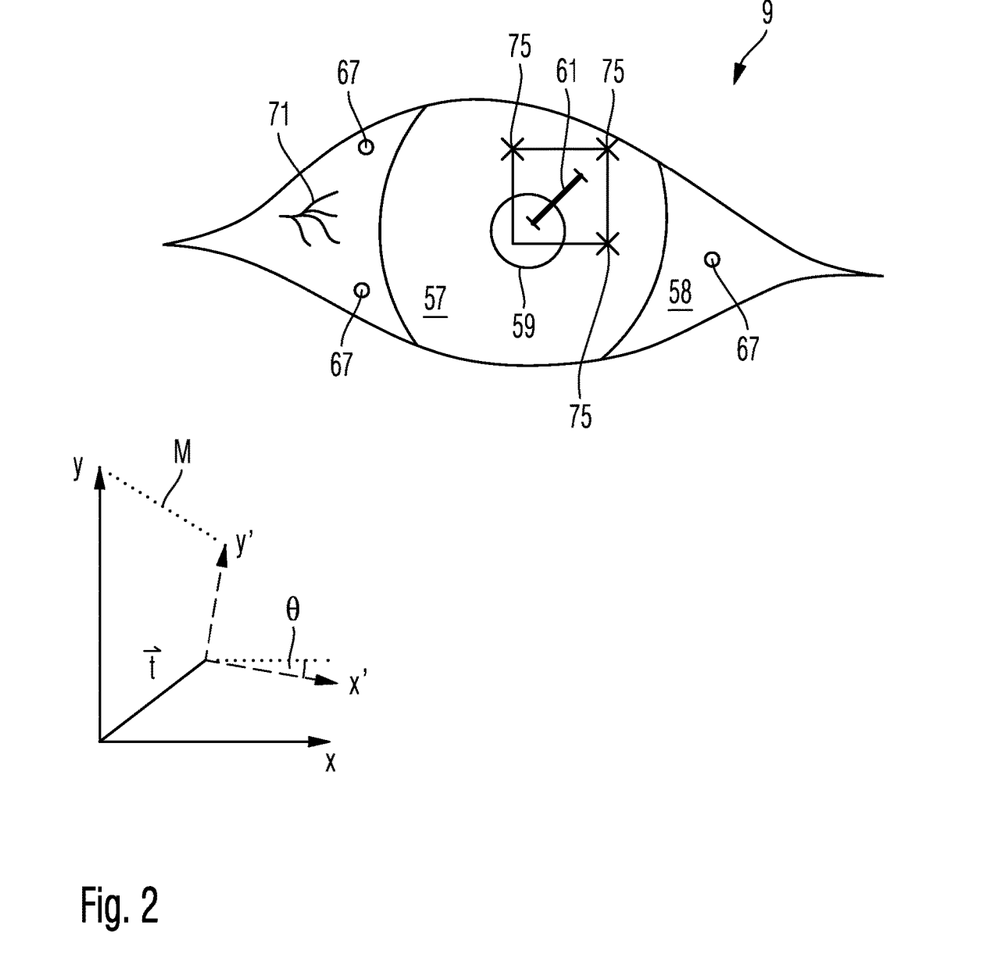
FIG. 2 is a schematic illustration of an eye for explaining geometric relations of an OCT B-scan performed on the eye.

FIG. 2 is a schematic representation of an elevational view of the eye and shows an iris 57, a sclera 58 and a pupil 59. Line 61 in FIG. 2 represents a B-scan line on the cornea of the eye along which the previous (first) B-scan was performed. It is now desired to generate a representation of a B-scan performed along the same line 61. Herein, the placement of the previous B-scan relative to the eye is not only defined by the scan line 61 since planes of two B-scans may be performed along two identical scan lines while they are tilted relative to each other. Therefore, the displayed desired B-scan should not only extend along the scan line 61 but should also be oriented along a same plane as the previous (first) B-scan.

The surgical microscope 3 is operated as an eye tracker, i.e. as a system which is able to detect the placement of the eye relative to the system with respect to plural degrees of freedom. For this purpose, the controller 21 analyzes detected images of the eye. FIG. 2 shows structures of the eye which are detectable in the images and on which the analysis can be based. Using the eye tracker, the placement of the eye 9 relative to the ophthalmologic system 1 can be determined with respect to some or all degrees of freedom. Based on the detected placement of the eye relative to the ophthalmologic system, the current placement of the eye can be changed according to the detected degrees of freedom in order to adapt the placement of the eye such that the placement better conforms with the placement the eye had relative to the OCT system having performed the previous B-scan. For this purpose, the placement of the eye is changed relative to a reference placement of the OCT system 31 based on the data representing the placement of the eye relative to the OCT system having performed the previous B-scan. The reference placement of the OCT system 31 may be defined, for example, by the OCT measuring light beam directed onto the eye when the scanning mirror rests in its non-deflected null position.

The controller 21 may operate an actuator 63 in two spatial directions (x, y) as indicated by arrows 65 in FIG. 1 in order to change the position of the eye relative to the OCT system. For example, the actuator 63 may change a configuration of a stand carrying the ophthalmologic system 1 in order to displace the ophthalmologic system in the two spatial directions. Moreover, the actuator 63 may displace a support on which the patient is resting in the two directions 65. Moreover, the actuator 63 may change a position at which the deflecting mirror 43 is located in front of the objective lens, or a null position of the scanning mirror 47 can be changed in order to change the reference placement of the OCT system relative to the eye 9.

In order to perform a B-scan such that its placement relative to the eye corresponds to the placement of the previous B-scan relative to the eye, it is necessary to know the arrangement of the eye relative to the OCT system for performing the next B-scan. The placement of the eye 9 relative to the ophthalmologic system 1 can be adjusted with respect to plural degrees of freedom as illustrated below with reference to FIGS. 2 and 3.

FIG. 2 schematically shows an image of the eye 9 as it can be detected by the camera 13, for example. FIG. 2 further shows a coordinate system with axes x and y corresponding to the coordinate system of the OCT system 31, wherein the axes x and y are orthogonal to each other and orthogonal to a direction of the OCT measuring beam. The eye 9 can be positioned relative to the OCT system with respect to the two degrees of freedom x-position and y-position. In this coordinate system, the eye may have changed its placement relative to the previous B-scan. This is indicated in FIG. 2 by a translation vector $\vec{t}$ and a rotational angle θ, wherein the axes x' and y' represent the coordinates of the coordinate system of the OCT system during the previous B-scan. A corresponding change of the coordinate system also occurs when the previous B-scan was performed using a different OCT system. The axes x' and y' then represent the coordinate system of the other OCT system. Apart from the translation and rotation, the placement of the eye relative to the OCT system may also have changed with respect to a further degree of freedom which is a magnification. The change in magnification is illustrated in FIG. 2 by a factor M representing a change in a unit length between coordinates x and x'. Such change in magnification may be caused, for example, by a change of the distance of the eye 9 from the ophthalmologic system. Such change in magnification may be further caused by the fact that the OCT system having performed the previous B-scan is different from the OCT system 31 of the ophthalmologic system 1 used for performing the next B-scan.

As mentioned above, the ophthalmologic system 1 includes an eye tracker comprising the camera 13. Images recorded by the camera are analyzed by the controller 21 in order to determine the parameters x-position, y-position, rotation and magnification. This analysis is based on an identification and analysis of structures which are detectable in the images of the anterior portion of the eye. This structures include the pupil 59, blood vessels 71 and the sclera 58. It is also possible to apply dye markers 67 on the sclera wherein the dye markers are detectable in the images such that the image analysis is facilitated. The data representing the placement of the previous B-scan relative to the eye may comprise an image of the eye recorded by the camera of the ophthalmologic system 1. This image is sufficiently similar to the currently detected image. The placement of the eye relative to the ophthalmologic system can be determined and represented, for example, by the parameters x-position, y-position, rotation and magnification. When the placement of the B-scan 61 (see fi FIG. 2) relative to the eye of the previous B-scan is known, a B-scan line to be used for the next B-scan can be determined by using the function of the eye tracker alone. The correspondence of the scan lines of two B-scans does, however, not completely define the placement of the next B-scan with respect to all possible degrees of freedom.

Figure 3:
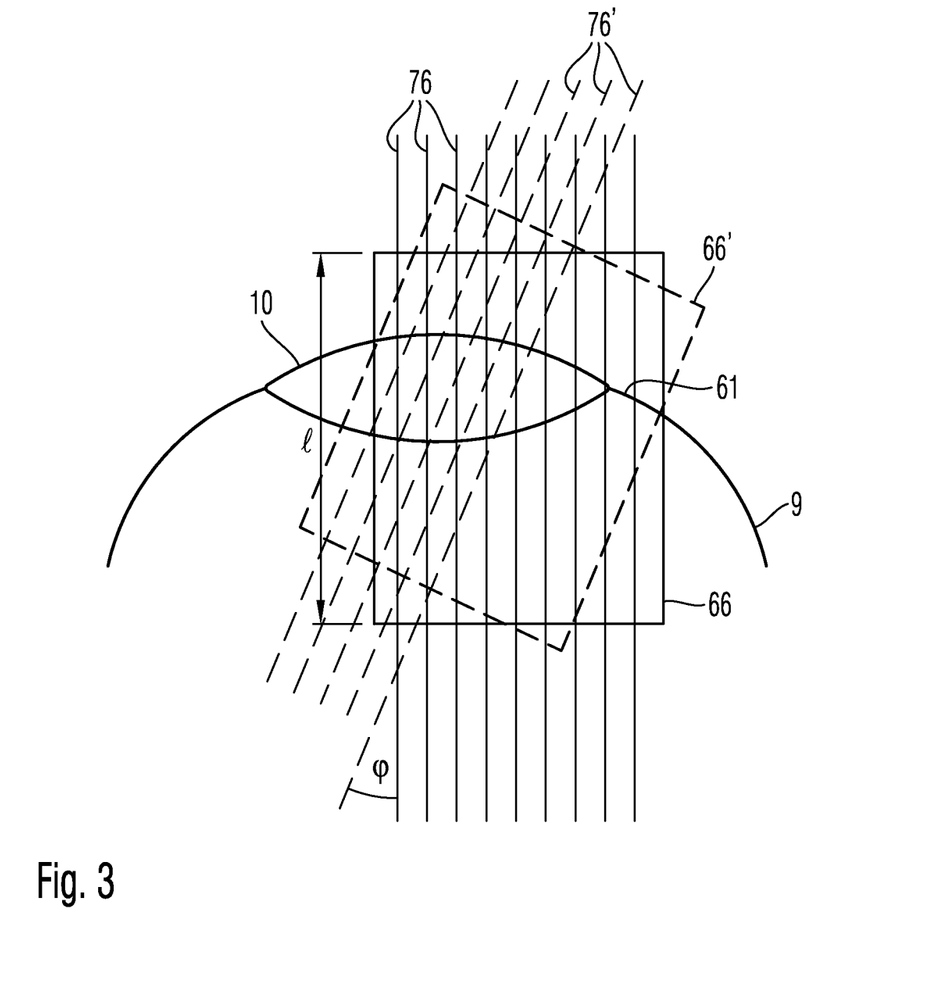
FIG. 3 is a further schematic illustration of an eye explaining geometric relations of an OCT B-scan performed on the eye.

FIG. 3 is a schematic sectional illustration of the eye 9 and of two B-scans. The rectangle 66' shown in broken lines presents a portion of a plane of the previous B-scan, and a rectangle 66 shown in full lines represents a portion of a plane of a B-scan performed using the OCT system 31 if the placement of the eye 9 is not adjusted with respect to a further degree of freedom to the placement of the previous B-scan relative to the eye. Those B-scans extend along the scan line 61 on the surface of the eye and they extend in a same plane. Lines 76 and 76' in FIG. 3 represent directions of A-scans in the respective B-scan. It is apparent that the full lines 76 representing the A-scans of the currently performed B-scan are oriented at an angle φ different from zero relative to lines 76' indicating the directions of the A-scan forming the previous B-scan 66'. The two B-scans are tilted relative to each other, accordingly. Such tilt is possibly not detectable using the eye tracker based on the detection of images of the anterior portion of the eye.

In the illustration of FIG. 3, the planes 66 and 66' of the two B-scans are tilted relative to each other and are located in the drawing plane of the Figure. Moreover, these planes can be tilted relative to each other in orthogonal directions while they still intersect at the straight scan line 61. In this explanation, the scan line formed on the surface of the eye is assumed to be a straight line, while, in practice, the line will be curved due to the curvature of the eye. However, this curvature can be ignored for facilitating the present illustration. It is apparent that the placement of the eye relative to the OCT system can be defined with respect to further degrees or freedom which may be represented by two parameters indicating a tilt in two different directions.

The ophthalmologic system 1 uses the OCT system 31 for detecting such tilt.

The extension of the B-scans in their depth direction, i.e. the length l (see FIG. 3) of the A-scans, is determined by the configuration of the interferometer 53. By changing, for example, a focal length of the lens 41 or by changing other parameters of the ophthalmologic system 1, such as the actuators 63 of the stand, it is possible to adjust the OCT system relative to the eye such that the performed A-scans reach at least partially into the eye 9.

Plural A-scans can be used to detect characteristic structures of the eye, such as, for example, the surface of the cornea 10. The depth within the respective A-scan at which the characteristic structure is detected represents the distance of that structure from the OCT system 31.

The controller 21 may perform, for example, A-scans at three different A-scan positions 75 (see FIG. 2) which are located close to the scan line 61 in order to determine the tilt illustrated with reference to FIG. 3 above. Assuming that the surface of the cornea has a spherical shape or that the shape of the surface of the cornea is known from previous measurements, the illustrated tilt of B-scans can be determined based on the at least three A-scans performed at the at least three A-scan positions 75. In order to adjust the placement of the next B-scan relative to the eye to the placement of the previous B-scan also with respect to the two degrees of freedom representing the tilt, it would be possible to operate the actuators 63 such that the OCT system is oriented relative to the eye such that the orientation of the OCT system relative to the eye is the same as during the previous B-scan. Subsequent to such orientation and positioning of the OCT system relative to the eye, the next B-scan can be performed by scanning the OCT measuring beam along the B-scan line and performing A-scans at plural different positions of the OCT measuring beam along the B-scan line.

In addition to the three A-scan positions 75 illustrated above, further A-scans can be performed at additional A-scan positions. For example, two or more B-scans can be performed, each including plural A-scans, wherein the scan lines of these B-scans are not too distant from the B-scan line 61 of the desired next B-scan. For example two B-scans can be performed along the two lines connecting the three A-scan positions 75 shown in FIG. 2. This allows to determine the placement of the eye also with respect to the tilt at a higher accuracy. The at least three scan positions 75 or the B-scan lines of the two or more B-scans can be determined based on the data representing the placement of the previous B-scan relative to the eye. It is then in particular possible to ensure that the at least three A-scan positions 75 and the B-scans lines of the two or more B-scans are close to the B-scan line 61 of the previous B-scan. It is, however, also possible to determine the at least three A-scan positions 75 or the scan lines of the two or more B-scans independently of the data representing the placement of the previous B-scan relative to the eye as long as they are located within the sclera 58, iris 57 or pupil 59 since these measurements are suitable for determining the placement of the eye relative to the OCT system with a sufficiently high accuracy. For example, the at least three A-scan positions or the scan lines of the two or more B-scans can be determined based on the placement of the eye relative to the ophthalmologic system as determined using the eye tracker.

The positioning and orienting of the OCT system relative to the eye such that the placement of a performed B-scan is the same as in a previously performed B-scan, wherein the placement includes also the degrees of freedom of the tilt, may require sometimes large movements of the OCT system relative to the eye if the orientation of the eye within the eye socket of the patient has changed due to manipulations performed during the surgery. It is then not easily possible to perform the next B-scan and to generate a representation of such next B-scan such that the placement of the representation of the B-scan relative to the eye is the same as in the previously performed B-scan.

A method will be illustrated below allowing to generate a representation of a B-scan having a substantially same placement relative to the eye as a previously performed B-scan without performing exactly this B-scan the representation of which is generated. In the perspective representation of FIG. 4, a plate 81 represents the entirety of data elements 84 of the previously performed B-scan. The data elements are arranged in a two-dimensional rectangular array having columns 82, wherein each column 82 includes the data elements 84 of one A-scan. The A-scans 82 are arranged adjacent to each other along B-scan line 83. Each data element 84 is associated with a measured reflectivity or scattering probability at a location corresponding to the location of the data element 84 in the plate 81. A representation of the B-scan 81 as a two-dimensional image can be generated by displaying pixels of the image at brightness values determined based on the associated reflectivities or scattering probabilities of the respective data elements 84. Due to the limited spatial resolution of the OCT system and the finite distance between adjacent A-scans 82 along the scan line 83, the data elements 84 each represent a reflectivity or scattering probability within a measuring volume which can be represented as a cuboid having edges of lengths determined by the resolution of the OCT system and the distance of adjacent A-scans from each other.

Figure 4:
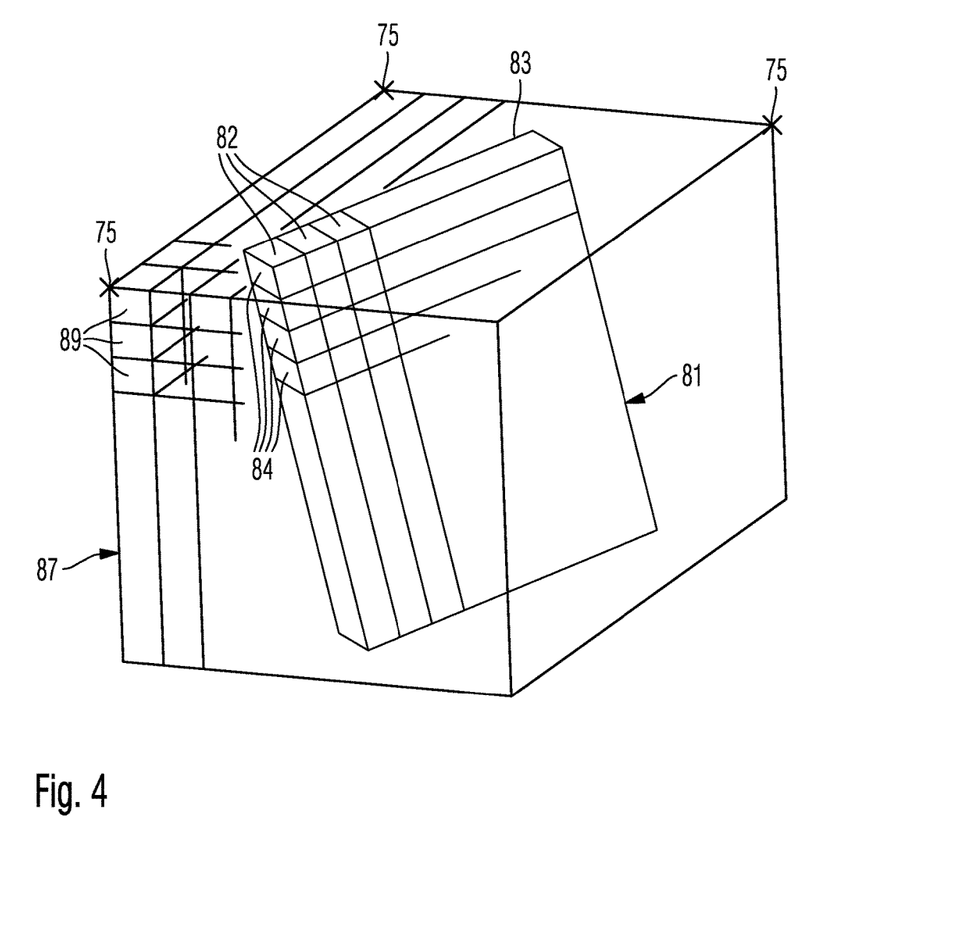
FIG. 4 is a schematic illustration of data elements of OCT scans.

In order to generate a representation of a next B-scan without performing this B-scan, a plurality of A-scans is performed within a volume represented as a cuboid 87 in FIG. 4. The plate 81 of data elements of the previously performed B-scan is contained within the cuboid 87, wherein the plate 81 is tilted relative to edges of the cuboid 87. The cuboid 87 can be selected such that three corner points of the cuboid are located at positions where the A-scan positions 75 of FIG. 2 are located. The corner points of the cuboid 87 are selected such that the previous B-scan 81 is at least partially located within the cuboid 87. A plurality of A-scans are performed at a plurality of A-scan positions within an upper surface of the cuboid 87 of FIG. 4. The A-scan directions, i.e. the orientation of the depth profiles of the reflectivity measured by the A-scans correspond to the vertical direction in the representation of FIG. 4. The A-scan positions at the upper surface of the cuboid 87 in FIG. 4 can be, in particular, selected such that the A-scan positions are arranged in a regular rectangular array. This will simplify the subsequent calculations. It is, however, also possible to deviate from the regular rectangular array of A-scan positions and to use other arrangements of A-scan positions. Using the regular rectangular array of A-scan positions allows, in particular, to perform a plurality of B-scans, using the OCT system, along B-scan lines located adjacent to each other. The data obtained by such B-scans may represent reflectivities or scattering probabilities within volumes represented as cuboids 89 in FIG. 4. The dimensions of these cuboids 89 are defined by the resolution of the OCT system, the distance between adjacent A-scan positions along the B-scan lines and the distance between adjacent B-scan lines. The data elements 89 may also be referred to as voxels.

In order to generate a representation of a B-scan having a placement relative to the eye corresponding to the previously performed B-scan 81, it is necessary to determine measuring values of the refractivities or scattering probabilities associated with the data elements 84. This is not directly possible since the exactly same B-scan is not performed again. However, the data elements 89 of the cuboid 87 are associated with actually measured reflectivities or scattering probabilities, and the cuboid 87 contains the previously performed B-scan 81. It is thus possible, to assign a value of the reflectivity or scattering probability to each data element 84, wherein the respective value is determined based on data elements 89 associated with actually measured values. The set of data elements 89 contributing to the determination of the values of each data element 84 is formed of data elements 89 located close to the respective data element 84. For example, each data element 84 can be assigned the value of the voxel 89 having the largest spatial overlap with the respective data element 84. It is further possible, to assign a value to each data element 84 calculated as an average of the values of all voxels 89 overlapping with the respective data element 84. For this purpose, the values of the voxels 89 contributing to the average can be weighted, for example by a weighting factor which increases with increasing spatial overlap between the voxel 89 and the data element 84.

It is, therefore, possible to generate the representation of a new B-scan having a same placement relative to the eye as a previously performed B-scan without actually performing the new B-scan. For this purpose, a plurality of A-scans is performed in a hull volume containing the desired B-scan. The representation of the desired B-scan is generated from measurement values obtained from locations within the larger hull volume.

In the ophthalmologic system 1 illustrated above, the microscope 3 is used as an eye tracker by analyzing images obtained by the camera 13 of the microscope 3 in order to determine a placement of the eye relative to the OCT system with respect to at least some degrees of freedom. The placement of the eye can be determined with respect to additional degrees of freedom, in particular degrees of freedom which can be represented as a tilt, by performing the at least three A-scans. It is, however, also possible to use other types of eye trackers in the ophthalmologic system 1 in order to determine the placement of the eye relative to the OCT system with respect to at least some or all degrees of freedom. It can then be possible to omit the performing of the at least three A-scans for determining the placement of the eye relative to the OCT system with respect to the additional degrees of freedom including the degrees of freedom which can be represented by a tilt. It is then possible to perform the at least one third B-scan in order to generate the representation of the desired second B-scan. Of course, the performing of the plurality of A-scans within the hull volume containing the second B-scan includes the performing of the at least three A-scans.

While the disclosure has been described with respect to certain exemplary embodiments thereof, it is evident that many alternatives, modifications and variations will be apparent to those skilled in the art. Accordingly, the exemplary embodiments of the disclosure set forth herein are intended to be illustrative and not limiting in any way. Various changes may be made without departing from the spirit and scope of the present disclosure as defined in the following claims.

The invention claimed is:

1. A method of operating an ophthalmologic system comprising an eye tracker and an OCT system, wherein the method comprises:
   providing data representing a placement of a first B-scan performed on an eye relative to the eye;
   performing a measurement on the eye using the eye tracker;
   determining a placement of the eye relative to the ophthalmologic system based on the measurement using the eye tracker;
   placing the eye relative to a reference placement of the OCT system based on the provided data and the determined placement;
   performing A-scans on the eye at at least three A-scan positions, wherein the at least three A-scan positions are not arranged on one straight line;
   determining a placement of a second B-scan relative to the OCT system based on at least one of the at least three A-scans and the provided data such that the second B-scan and the first B-scan have a substantially same placement relative to the eye; and
   generating a representation of the second B-scan,
   wherein the generating of the representation of the second B-Scan comprises displaying of scattering intensities at a plurality of locations, wherein the representation of the scattering intensity at each given location of the plurality of locations is based on a subset of measured scattering intensities obtained by the plurality of A-scans, wherein the scattering intensities of the subset are measured at locations having a distance from the given location smaller than a predetermined distance.

2. The method according to claim 1, wherein in the second B-scan is not oriented parallel to anyone of straight lines connecting any pair of the at least three A-scan positions.

3. The method according to claim 1 wherein the performing of the A-scans at the at least three A-scan positions comprises performing of at least two B-scans which do not extend parallel to each other and which, in particular extend orthogonally relative to each other.

4. The method according to claim 1, further comprising performing of a third B-scan having a substantially same placement relative to the eye as the second B-scan, wherein the generating of the representation of the second B-scan comprises generating a representation of the at least one third B-scan.

5. The method according to claim 1, wherein the A-scans are placed within a hull volume which at least partially includes the second B-scan, wherein the hull volume is the convex hull of the A-scans.

6. The method according to claim 5, wherein the hull volume has a shape of a cuboid.

7. The method according to claim 6, wherein the second B-Scan is not oriented parallel to anyone of the surfaces of the cuboid.

8. The method according to claim 1, wherein the generating of the representation of the scattering intensity at the given location comprises averaging of the scattering intensities of the subset of measured scattering intensities.

9. The method according to claim 1, wherein the predetermined distance is less than 10 times of an average distance between adjacent A-scan positions.

10. The method according to claim 1, wherein the eye tracker comprises a surgical microscope and a camera, and
   wherein the determining of the placement of the eye relative to the ophthalmologic system is based on images detected by the camera.

11. The method according to claim 1, wherein the data representing the placement of the first B-scan relative to the eye represent the placement relative to the eye with respect to at least four degrees of freedom, wherein the degrees of freedom can be represented by plural parameters selected from a group of parameters comprising a position in an x-direction, a position in a y-direction, a rotation, a scaling and a tilt.

12. The method according to claim 11, wherein the placement of the eye relative to the ophthalmologic system determined by the measurement using the eye tracker is determined with respect to at least three degrees of freedom.

13. The method according to claim 12, wherein the at least three degrees of freedom can be represented by the position in the x-direction, the position in the y-directional, the rotation and the magnification.

14. The method according claim 11, wherein the placement of the eye relative to the ophthalmologic system determined based on the at least three A-scans is determined with respect to at least one degree of freedom which can be represented by a tilt.

15. An ophthalmologic system configured to perform the method according to claim 1.

* * * * *

UNITED STATES PATENT AND TRADEMARK OFFICE
CERTIFICATE OF CORRECTION

PATENT NO. : 9,883,796 B2
APPLICATION NO. : 14/873337
DATED : February 6, 2018
INVENTOR(S) : Günter Meckes et al.

Page 1 of 1

It is certified that error appears in the above-identified patent and that said Letters Patent is hereby corrected as shown below:

In the Specification

Column 5, Line 60, "on interferometer" should read --an interferometer--.

Column 8, Line 46, "see fi FIG. 2" should read --see FIG. 2--.

Column 9, Line 66, "B-scans lines" should read --B-scan lines--.

Column 11, Lines 9 and 10, "cuboids 89" should read --cuboids 87--.

In the Claims

Column 12, Line 45, Claim 2, "wherein in the" should read --wherein the--.

Column 14, Line 10, Claim 13, "y-directional" should read --y-direction--.

Column 14, Line 12, Claim 14, "according claim" should read --according to claim--.

Signed and Sealed this
Twenty-fourth Day of July, 2018

Andrei Iancu
*Director of the United States Patent and Trademark Office*